United States Patent [19]
Wiest et al.

[11] Patent Number: 5,342,294
[45] Date of Patent: Aug. 30, 1994

[54] GAS CONNECTION DEVICE FOR INSUFFLATION EQUIPMENT

[76] Inventors: Peter P. Wiest, Hessenallee 8, D-1000 Berlin 19; Richard Korejwo, Borstellstr. 36, D-1000 Berlin 41, both of Fed. Rep. of Germany

[21] Appl. No.: 922,812

[22] Filed: Jul. 31, 1992

[51] Int. Cl.$^5$ ............................................. A61M 37/00
[52] U.S. Cl. .................... 604/26; 128/747; 137/613
[58] Field of Search .................... 604/23–26; 128/747, 748; 137/492.5, 613

[56] References Cited

U.S. PATENT DOCUMENTS

| | | | |
|---|---|---|---|
| 2,059,500 | 11/1936 | Thomas | 604/26 |
| 2,337,347 | 12/1943 | McPherson | 604/26 |
| 3,885,590 | 5/1975 | Ford et al. | 604/26 |
| 3,957,033 | 5/1976 | Winchell et al. | 604/26 |
| 4,207,887 | 6/1980 | Hiltebrandt et al. | 604/26 |
| 4,258,721 | 3/1981 | Parent et al. | 604/26 |
| 4,361,138 | 11/1982 | Kinoshita | 604/26 |
| 4,702,277 | 10/1987 | Ollivier | 137/613 |
| 4,705,073 | 11/1987 | Beck | 604/26 |
| 4,757,836 | 7/1988 | Marchal | 137/492.5 |
| 4,782,861 | 11/1988 | Ross | 137/613 |
| 4,919,895 | 4/1990 | Heldebrant et al. | 604/26 |
| 5,061,239 | 10/1991 | Shiels | 604/26 |

*Primary Examiner*—Ralph Lewis
*Attorney, Agent, or Firm*—McGlew and Tuttle

[57] ABSTRACT

The invention relates to a gas connection device for insufflation equipment, in particular for mini-invasive surgery as well as laparoscopy and hysteroscopy. The invention includes a connection port 3 for the gas supply, a pressure reducer 4, a safety valve 5, a gas outlet port 7 provided with a solenoid vane 6, and a manometer 8.

In order to have an economic assembly of all components of the gas connection device pre-assembled in an insufflation device, it is provided, according to the invention, that the connection port 3, the pressure reducer 4, the safety valve 5, the solenoid valve 6, with the gas outlet port 7, and the manometer 8 are connected to a common metal main body 1, and are connected to a common metal main body 1, and are connected with main body 1. Therefrom simultaneously results, by the loosenable and replaceable installation of the connection port 3 in the main body 1, the possibility to perform, after the final assembly of the insufflation device, an adaption of the connection port to the requirements of the gas bottle connection (FIG. 1).

7 Claims, 4 Drawing Sheets

GAS CONNECTION DEVICE FOR INSUFFLATION EQUIPMENT

FIELD OF THE INVENTION

The invention relates to a gas connection device for insufflation equipment. The gas connection device serves for connecting a medical insufflation device, in particular for the mini-invasive surgery as well as laparoscopy and hyteroscopy, to a gas stock bottle, and for reducing the gas bottle pressure to the allowable operating pressure of the insufflation device (e.g. 50 mm Hg) as well as for monitoring, measuring and controlling the operating pressure of the insufflation gas leaving the gas outlet of the gas connection device.

BACKGROUND OF THE INVENTION

In a prior art embodiment of the gas connection device of a conventional insufflation device, the outlet port is mounted in the device wall, and is connected, over a copper pipe, with the pressure reducer. The latter is connected, over a pressurised-air hose, with the safety valve, and over another copper pipe, with a pressure-indicating manometer. Finally, another pressurised-air hose is present between the safety valve and the solenoid valve. The copper pipes and the pressurised-air hoses are connected over screwed joints with special cap nuts, to the respective components of the gas connection device. Thereby, when mounting the prior art gas connection device within the housing of an insufflation device, several individual assemblies have to be installed, and have to be connected with each other over copper pipes and pressurised-air hoses. Processing of the copper pipes requires an enormous expenditure by cutting, bending, chromating, removal of chips and the like. Further, considerable costs are caused by stocking and purchasing the copper pipes, pressurised-air hoses, screwed joints and cap nuts. In total, there are relatively high assembly costs and a large number of potential failure locations.

SUMMARY AND OBJECTS OF THE INVENTION

It is therefore the object of the invention to provide a gas connection device for insufflation equipment of the aforementioned species, which is simplified with respect to shorter assembly times, reduction of the number of components and failure locations and lower purchasing and stocking costs.

For the solution of this object, the invention provides that the connection port, the pressure reducer, the safety valve and the solenoid valve; with the gas outlet port, are connected to a common main body, and are connected with each other by channels formed inside the main body. The main body, in particular formed of metal, is pre-assembled prior to installation in the housing of the insufflation device, the pressure reducer, the safety valve and the solenoid valve, provided with the gas outlet port, are already connected with the respective channels formed in the main body, and are fixedly attached at the main body. Subsequently, the thus pre-assembled and tested gas connection device is fixedly attached at the device wall of the insufflation device. Finally, the gas outlet port is brought into the main body of the gas connection device, from outside through the device wall. The gas connection device according to the invention requires only half the number of components, which are necessary for the conventional gas connection device.

In a particularly preferred manner, the connection port is disposed loosenably and replaceably in the main body. Thereby, the connection port can easily be adapted to various constructions of a gas stock bottle, such as cartridge-type, pin, index, American $CO_2$, German $CO_2$, Japanese $CO_2$ and German $NO_2$ ports. Therefrom results the possibility of replacement of the various connection ports for the gas supply, without the insufflation device itself having to be dismounted. Further, by avoiding the formerly used gluing process of the individual components, defined sealing conditions will result, thereby maintenance of the insufflation device being improved. The compact assembly of the connection port for the gas supply, of the pressure reducer, the safety valve and a pressure monitor in a one-piece main body, and the connection of the components by channels formed in the main body, allows avoiding copper pipe connections and pressurised-air hoses between the individual components. Thereby, failure sources are eliminated, with regard to an improvement of quality, and considerable savings of copper pipe and the processing therefor, such as cutting, bending, chromating, removal of chips etc., are possible. Further savings result from the avoidance of screwed joints with corresponding cap nuts, thus stocking and purchasing as well as administration costs being reduced. Finally, there is no need to employ an additional device for preventing twisting of the gas connection. Considerably shorter assembly times and test possibilities of the gas connection device (gas connection combination) will be obtained, prior to installation in the insufflation device.

In the following, the gas connection device according to the invention for insufflation devices is described, based on an embodiment shown in the drawings.

DETAILED DESCRIPTION OF THE PREFERRED EMBODIMENT

Figure 1:
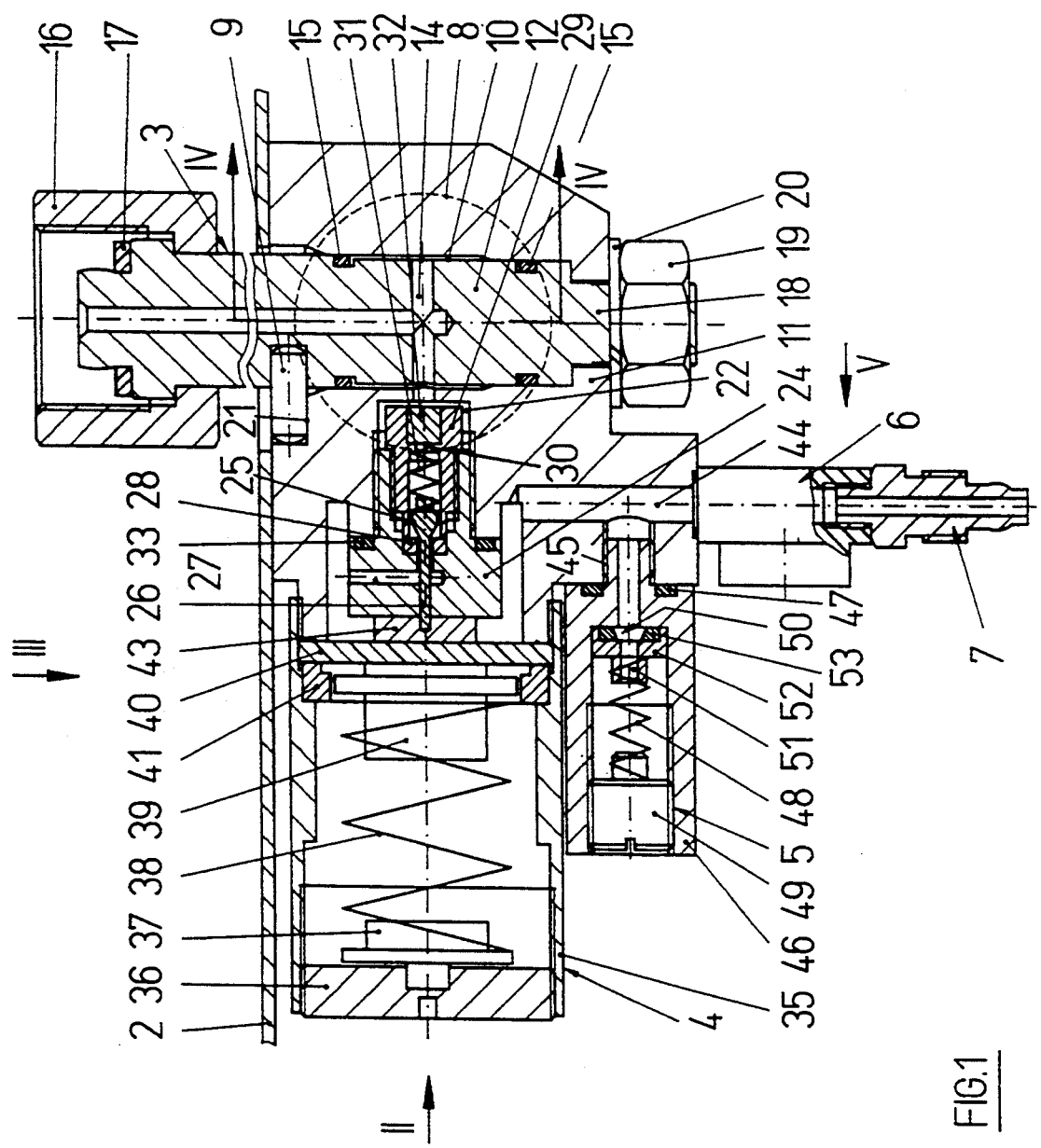
FIG. 1 a longitudinal section through the gas connection device.
Figure 2:
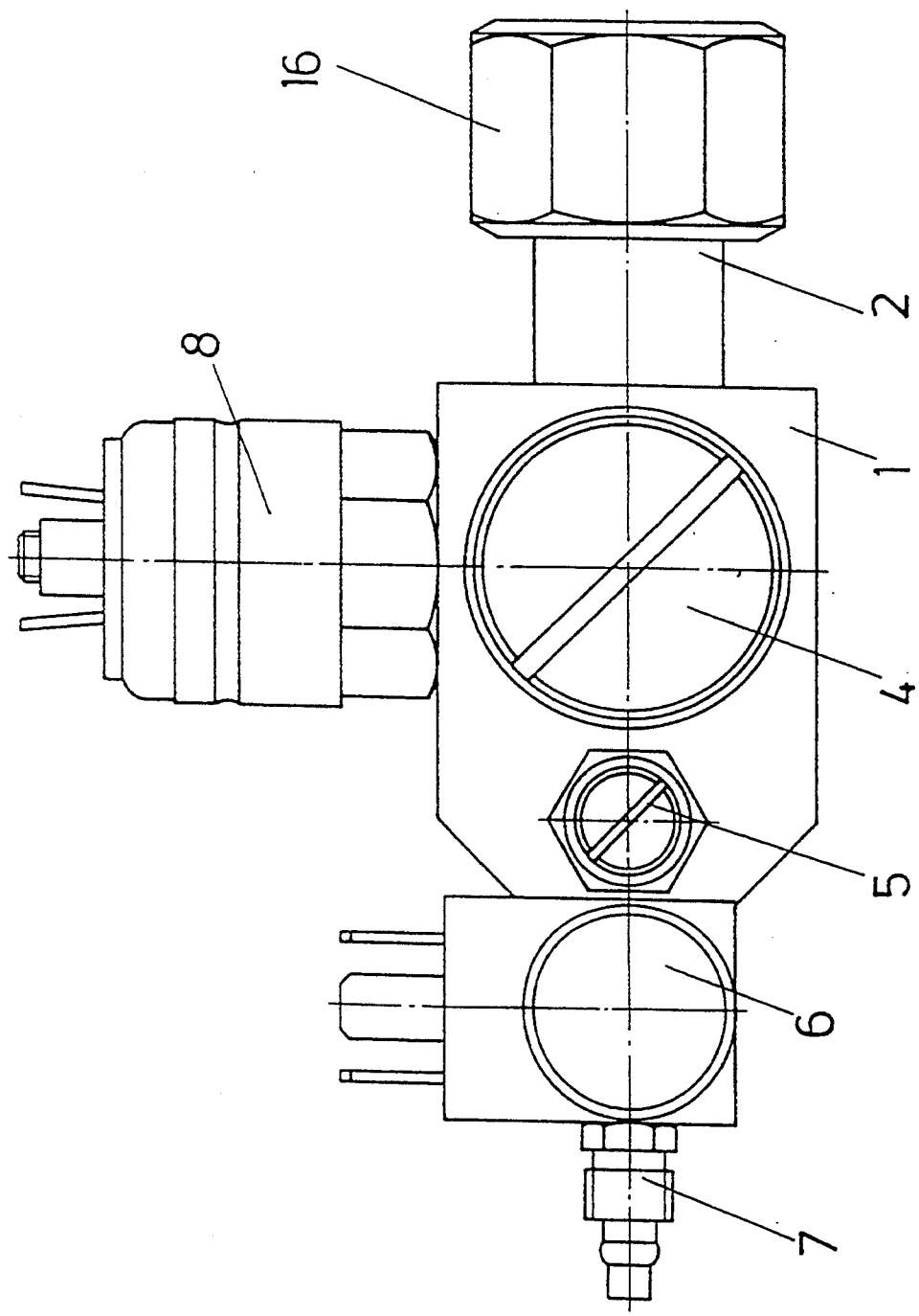
FIG. 2 a view according to arrow II in FIG. 1.
Figure 3:
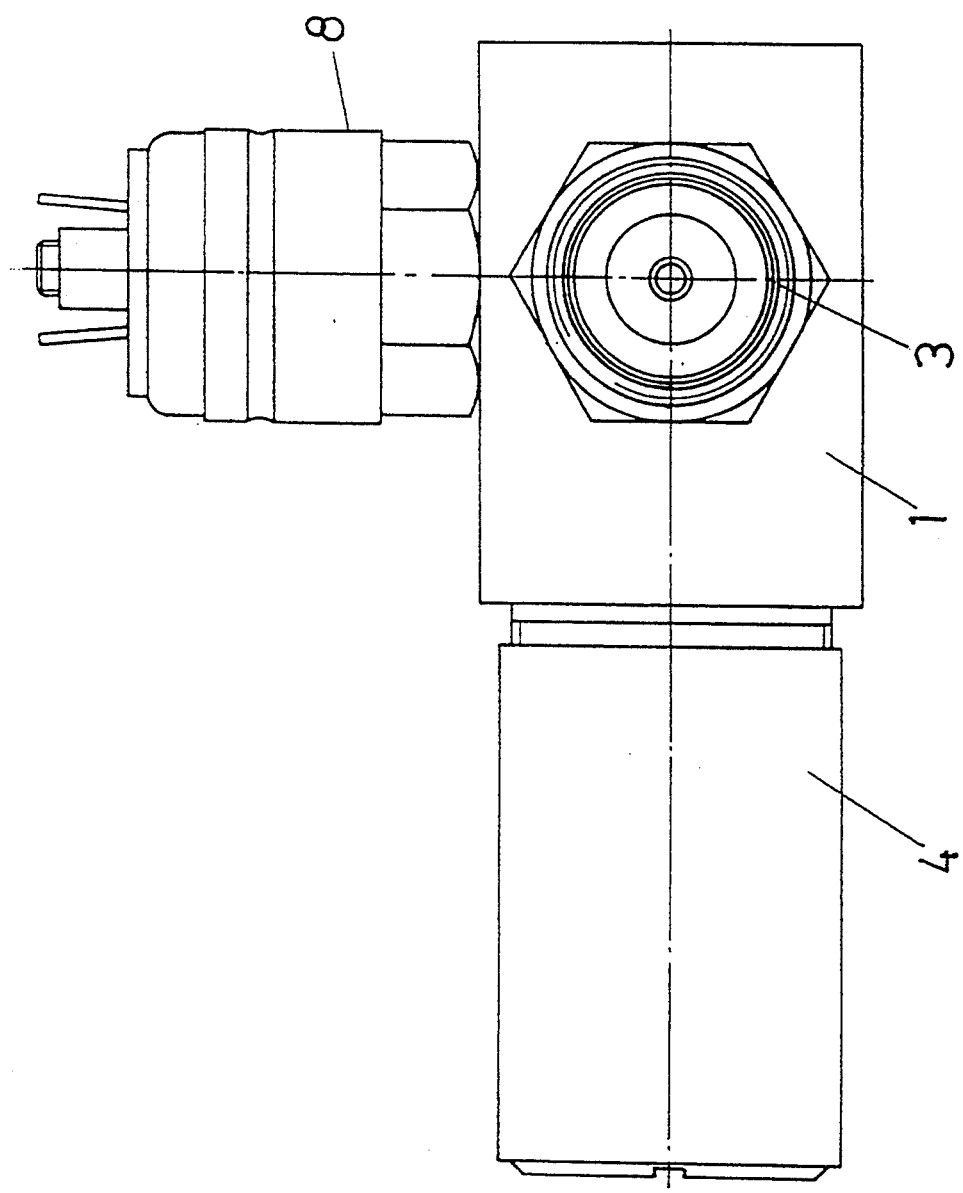
FIG. 3 a view according to arrow III in FIG. 1.
Figure 5:
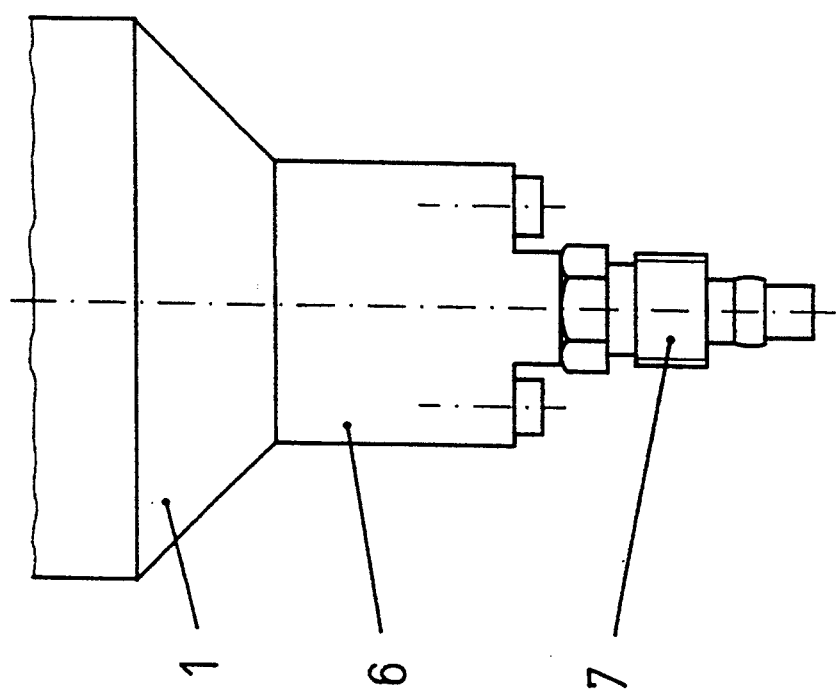
Figure 4:
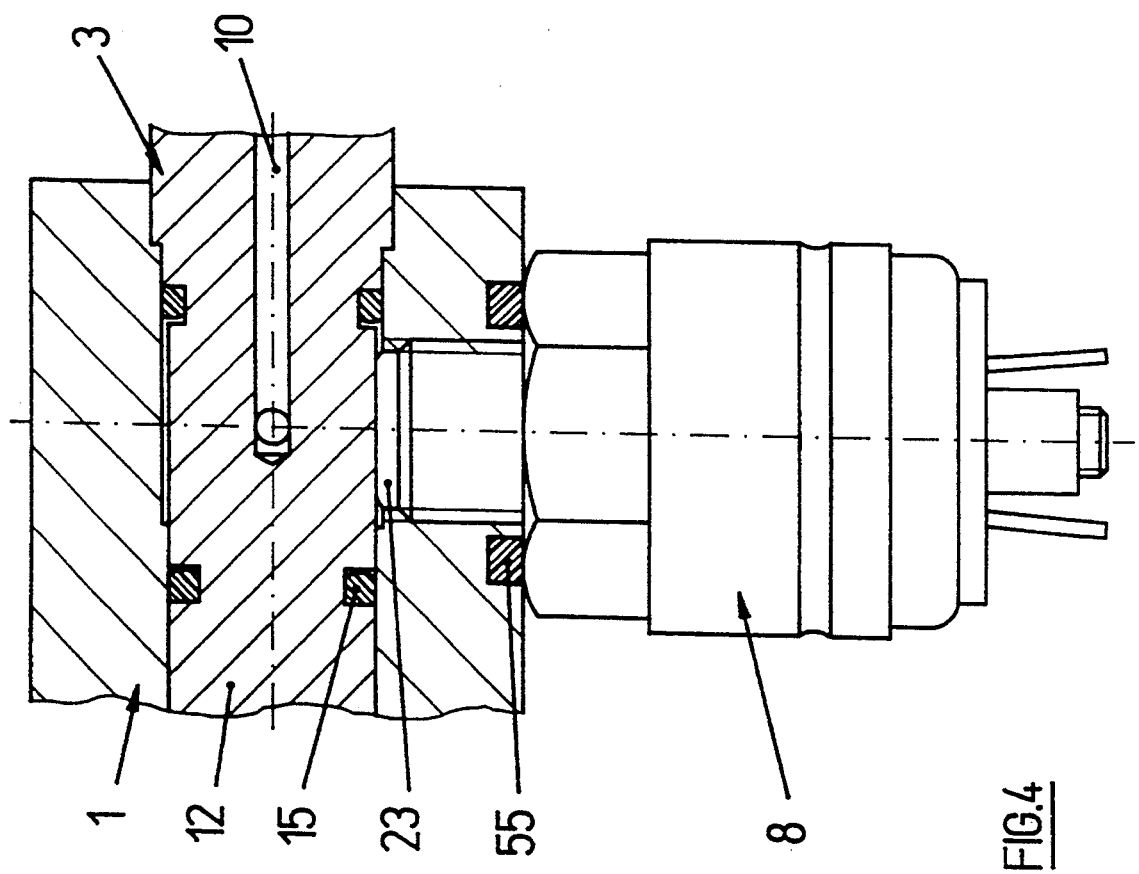
FIG. 4 a detailed section according to line IV—IV in FIG. 1, in an enlarged scale, and FIG. 5 a detailed view according to arrow V in FIG. 1.

The gas connection device for insufflation devices comprises a block-type, metal main body 1 fixedly attached, with a side face, to the device wall 2. A connection port 3, for the gas supply from a $CO_2$ stock bottle is loosenably and replaceably connected to the main body 1. On the left-hand side of the main body 1, in FIG. 1, is disposed a pressure reducer or regulator 4 with springs, a diaphragm and a needle valve for reducing and automatically adjusting delivery of the high stock pressure in the $CO_2$ gas bottle from, e.g., 70 bars to the operating pressure of 2 bars. Beside the pressure reducer 4, a safety valve 5 is provided, serving as an over-pressure protection. At a right angle to the safety valve 5, a solenoid valve 6 is located, with a gas outlet port 7 connected thereto. Vertically to the axes of the connection port 3 and of the pressure reducer 4, a manometer 8 is connected to the main body 1, as is shown in FIGS. 2 to 4. The manometer 8 is adapted as an electronic pressure monitor.

For receiving the connection port 3, a first channel 10 is adapted as a cylindrical borehole in the main body 1. At the end of the borehole, directed away from the device wall 2, is a circumferential collar 11 projecting inwardly. The connection port 3 abuts, at the front of the borehole. The connection port 3 itself is adapted as a cylindrical piece 12, and provided with a blind hole 13 and a through-hole 14 passing through the latter before the inner end thereof, and with seals 15 in the form of O-rings, disposed at the periphery of the cylindrical piece 12, before and behind the orifices of through-hole. The seals seal the central portion of the main channel 10 towards outside.

The cylindrical piece 12 of the connection port 3 is provided, at the external end, with connecting means or members in the form of a cap nut 16 and a seal 17, in order to establish the connection with the $CO_2$ gas stock bottle. The thus formed connecting members can be adapted as cartridge-type, pin-index, American $CO_2$, German $CO_2$, Japanese $CO_2$ or German $NO_2$ ports. The connection port 3 is provided, at the internal end, with loosenable fixing members or means in the form of a threaded extension 18, a cap nut 19 screwed thereonto, and a disc 20 disposed underneath. The threaded extension 18 passes through the internal opening of the collar 11 of the main body 1, and the connection port 3 is attached at the main body 1 by tightening the cap nut 19. By this design, the connection port 3 is replaceable, with the gas connection device being mounted in the housing of the insufflation device. For having a proper alignment of the through-hole 14 of the connection port 3, and also for the latter protected against twisting, a cylindrical pin 9 is radially inserted in the cylindrical piece 12 thereof. A radial groove 21 is provided in the main body 1 for receiving the pin 9. The protection against twisting of the connection port 3 is particularly important for the pin-index port, since simultaneously, a positioning of the gas bottle is performed.

The main channel 10 terminates in a first transverse channel 22 (FIG. 1) for receiving the pressure reducer 4, and vertically thereto, a second transverse channel 23 (FIG. 4) for receiving the manometer 8 in the form of an electronic pressure monitor. A threaded portion 24 is screwed into the transverse channel 22 provided with an internal thread. The threaded portion has an axial bore 26 for receiving a valve needle 25 and with a radial bore 27 terminating in a U-shaped pressure compartment 28. A pressure piece 29 is screwed into the front of the threaded portion 24 and directed towards the main channel 10. The pressure piece 29 has an axial bore 30. On one side of the axial bore 30 a compression spring 31 loads the valve needle 25, and on the other side of which, directed towards the main channel 10, a sintered bushing 32 is disposed. The threaded portion 24 is sealed, with its head section, by an O-ring 33, and is screwed into the main body 1.

The pressure reducer 4 comprises, further, a sleeve body 35 screwed onto the external thread of a threaded portion 34 of the main body 1 enclosing the pressure compartment 28. The sleeve body is closed, at the end, by an adjustable closure plug 36 screwed into an internal thread. The closure plug carries, on its internal side, a receiving body 37 for another compression spring 38. The other end of spring 38 is placed on a diaphragm 40, which is clamped-in between a ring 41 in the interior of the sleeve body 35 and the threaded extension 34 of the main body 1. On the side of the diaphragm 40 directed towards the main body 1, there is provided a disc 43, into which engages the valve needle 25. The pressure reducer 4 thus being adjustable, by the adjustable spring force of the compression spring 38, reduces the high pressure of the gas supplied over the connection port 3, to the operating pressure of the insufflation gas which is supplied, over the pressure compartment 28, to an outlet channel 44 in the main body 1. The outlet channel terminates in the solenoid valve 6, to which the gas outlet port 7 is connected, as is shown in FIG. 1. Immediately ahead of the solenoid valve 6 terminates a threaded bore 45 in the outlet channel 44, into which a safety valve 5 is inserted. The latter consists of a cylindrical valve body 46, which is screwed, by interposing an O-ring 47 at the front, into the threaded bore 45. A compression spring 48 extends between an adjustable spring-compression screw 49 and a valve body 50, which is formed of an internal support 51 and an external support 52 for an O-ring 53.

Finally, according to FIG. 4, the manometer 8 in the form of an electronic pressure monitor is screwed, with its -threaded extension 54, by interposing an O-ring 55, into the transverse channel 23 in the main body 1. The main channel 10 and the two transverse channels 22, 23 are in a pressure connection with each other in the area between the two seals 15 of the connection port 3.

In the summary the invention relates to a gas connection device for insufflation equipment, in particular for the mini-invasive chirurgy as well as the laparoscopy and hyteroscopy, comprises a connection port 3 for the gas supply a pressure reducer 4, a safety valve 5, a gas outlet port 7 provided with a solenoid valve 6, and a manometer 8.

In order to have an economic assembly of all components of the gas connection device pre-assembled in an insufflation device, it is provided, according to the invention, that the connection port 3, the pressure reducer 4, the safety valve 5, the solenoid valve 6, with the gas outlet port 7, and the manometer 8 are connected to a common metal main body 1, and are connected with each other by channels 10, 22, 23, 44 formed inside the main body 1. Therefrom simulataneously results, by the loosenable and replaceable installation of the connection port 3 in the main body 1, the possibility to perform, after the final assembly of the insufflation device, an adaptation of the connection port to the requirements of the gas bottle connection (FIG. 1).

We claim:
1. Insufflation equipment comprising:
   an integral main body defining a cylindrical main channel, a first transverse channel, a second transverse channel and an outlet channel, said first and second transverse channels being in communication with said cylindrical main channel;
   a connection port having an external cylindrical shape insertable axially into and in communication with said cylindrical main channel, said connection port being replaceably connected to said integral main body, said connection port having an external end with a connecting means for connecting to a fluid supply and an internal end with fixing means for connecting and separating said connection port with said integral main body, said connection port defines a blind hole axially leading from said external end and stopping inside said connection port, said connection port also defines a through-hole radially passing through said external cylindrical shape of said connection port and being in commu- nication with said blind hole, said through-hole also being in communication with said cylindrical main channel, said connection port including seal means for sealing an interface between said external cylindrical shape and said integral main body, said sealing means sealing an area around said through-hole;

a pressure reducer connected to said integral main body and having one portion in communication with said first transverse channel and having another end in communication with said outlet channel;

a safety valve connected to said integral main body and in communication with said outlet channel;

a solenoid valve connected to said integral main body and in communication with said outlet channel;

a gas outlet port connected to said solenoid valve, said solenoid valve opening and closing communication between said outlet channel and said gas outlet port;

said pressure reducer, said safety valve and said solenoid valve are interconnected by said outlet channel;

a manometer connected to said integral main body and in communication with said second transverse channel.

2. Insufflation equipment according to claim 1 wherein:

said fixing means includes a collar portion at said internal end of said main channel, a threaded extension on said cylindrical connection port and a cap nut screwable onto said threaded extension, said cap nut and said cylindrical connection port enclosing said collar portion.

3. Insufflation equipment according to claim 1 wherein:

said integral main body defines a radial groove;

said cylindrical connection port includes a cylindrical pin means extending radially from said cylindrical connection portion for engaging with said radial groove of said integral main body and holding said connection port against rotating with respect to said integral main body.

4. Insufflation equipment according to claim 1 wherein:

said integral main body includes an internal thread inside said first transverse channel;

said pressure reducer includes a threaded portion with thread means for threading into said internal thread of said first transverse channel, said threaded portion defining an axial bore and a radial bore in communication with said radial bore, said threaded portion including a needle valve received by said axial bore and a pressure piece screwed into a front of said pressure reducer, said pressure piece defining an axial bore and including a needle valve and a compression spring biasing said needle valve of said pressure piece, said pressure piece also including a sintered bushing position adjacent said axial bore of said threaded portion.

5. Insufflation equipment according to claim 4, wherein:

said pressure reducer includes a diaphragm biasing said needle valve of said threaded portion and also includes an adjustable spring means for adjusting a pressure on said diaphragm.

6. A gas connection device according to claim 1, further comprising:

a plurality of additional connection ports, each of said plurality of additional connection ports being replaceable for said connection port and having connection means for connecting to different fluid supplies.

7. A gas connection device comprising:

an integral main body defining a main channel, a first transverse channel, a second transverse channel and an outlet channel, said first and second transverse channels being in communication with said main channel;

a connection port insertable into said main channel, said connection port and said integral main body including fixing means for connecting and disconnecting said connection port from inside said main channel, said connection port having a connecting means for connecting to a fluid supply, said connection port defines a blind hole axially leading from said external end and stopping inside said connection port, said connection port also defines a through-hole radially passing through an external cylindrical shape of said connection port and being in communication with said blind hole, said through-hole also being in communication with said main channel, said connection port including seal means for sealing an interface between said external cylindrical shape and said integral main body, said sealing means sealing an area around said through-hole;

a pressure regulator means connected to said integral main body and for automatically adjusting a pressure of a delivered fluid to a predetermined value, said pressure regulator means having one portion in communication with said first transverse channel and having another end in communication with said outlet channel;

a safety valve connected to said integral main body and in communication with said outlet channel;

a solenoid valve connected to said integral main body and in communication with said outlet channel;

a gas outlet port connected to said solenoid valve, said solenoid valve opening and closing communication between said outlet channel and sad gas outlet port;

said pressure regulator means, said safety valve and said solenoid valve are interconnected by said outlet channel;

a manometer connected to said integral main body and in communication with said second transverse channel.

* * * * *